United States Patent
Larsen et al.

(10) Patent No.: US 10,435,339 B2
(45) Date of Patent: Oct. 8, 2019

(54) FCC FEED ADDITIVE FOR PROPYLENE/BUTYLENE MAXIMIZATION

(71) Applicant: Marathon Petroleum Company LP, Findlay, OH (US)

(72) Inventors: Nikolas Larsen, Findlay, OH (US); Jeff Sexton, Findlay, OH (US); Dave Lomas, Barrington, IL (US)

(73) Assignee: Marathon Petroleum Company LP, Findlay, OH (US)

( * ) Notice: Subject to any disclaimer, the term of this patent is extended or adjusted under 35 U.S.C. 154(b) by 0 days.

(21) Appl. No.: 15/976,296

(22) Filed: May 10, 2018

(65) Prior Publication Data
US 2018/0327335 A1   Nov. 15, 2018

Related U.S. Application Data

(60) Provisional application No. 62/505,196, filed on May 12, 2017.

(51) Int. Cl.
*C07C 4/06* (2006.01)
*C10G 11/18* (2006.01)

(52) U.S. Cl.
CPC ............... *C07C 4/06* (2013.01); *C10G 11/18* (2013.01); *C10G 2400/02* (2013.01); *C10G 2400/28* (2013.01)

(58) Field of Classification Search
CPC .................................... C07C 4/02; C07C 4/06
See application file for complete search history.

(56) References Cited

U.S. PATENT DOCUMENTS

| | | | |
|---|---|---|---|
| 3,364,134 A * | 1/1968 | Hamblin | C10G 47/00 208/111.1 |
| 4,422,925 A | 12/1983 | Williams et al. | |
| 4,624,771 A * | 11/1986 | Lane | C10G 11/18 208/113 |
| 5,328,591 A | 7/1994 | Raterman | |
| 5,389,232 A | 2/1995 | Adewuyi et al. | |
| 6,093,867 A | 7/2000 | Ladwig et al. | |
| 8,007,662 B2 * | 8/2011 | Lomas | C10G 11/18 208/108 |
| 8,685,232 B2 | 4/2014 | Mandal et al. | |
| 2008/0156696 A1 | 7/2008 | Niccum et al. | |

FOREIGN PATENT DOCUMENTS

EP      2047905      4/2009

OTHER PUBLICATIONS

Yasin et al. ("Quality and chemistry of crude oils", Journal of Petroleum Technology and Alternative Fuels vol. 4(3), pp. 53-63, Mar. 2013) (Year: 2013).*

(Continued)

*Primary Examiner* — Youngsul Jeong
*Assistant Examiner* — Jason Y Chong
(74) *Attorney, Agent, or Firm* — Schaffer, Schaub & MarriottLTD

(57) ABSTRACT

An injection of a small amount of sweet vacuum residue into an FCC feed consisting of sweet gas oil combined with shape selective catalyst additives technology improves propylene and butylene yields significantly.

4 Claims, 2 Drawing Sheets

(56) References Cited

OTHER PUBLICATIONS

Penn State ("Cut Points", https://www.e-education.psu.edu/fsc432/content/cut-points) (Year: 2018).*

The American Petroleum Institute Petroleum HPV Testing Group ("Heavy Fuel Oils Category Analysis and Hazard Characterization" Dec. 7, 2012, http://www.petroleumhpv.org/~media/PetroleumHPV/Documents/2012_12_10_December_7_2012_Heavy%20Fuel%20Oil%20CAD_Final_std.pdf) (Year: 2012).*

Increase gasoline octane and light olefin yields with ZSM-5, Refining Online, 5(5), <https://www.refiningonline.com/BASFCatalystsKB_Updated/crep/Tcrtoc.aspx>.

Fluid catalytic cracking and light olefins production, Hydrocarbon Publishing Company, 2011, <http://www.hydrocarbonpublishing.com/store10/product.php?productid=B21104&srchkey=>.

Zhang, Jinhong et. al., Multifunctional two-stage riser fluid catalytic cracking process, Springer Applied Petrochemical Research, Sep. 3, 2014, 395-400, 4(4), <https://www.ncbi.nlm.nih.gov/pmc/articles/PMC5012360/>.

Reid, William, Recent trends in fluid catalytic cracking patents, part V: reactor section, Dilworth IP, Sep. 3, 2014, <https://www.dilworthip.com/recent-trends-fluid-catalytic-cracking-patents-part-v-reactor-section/>.

Akah, Aaron et. al., Maximizing propylene production via FCC technology, SpringerLink, Mar. 22, 2015, 377-392, 5(4), <https://link.springer.com/article/10.1007/s13203-015-0104-3>.

Vogt, E.T.C et. al., Fluid catalytic cracking: recent developments on the grand old lady of zeolite catalysis, Royal Society of Chemistry, Sep. 18, 2015, 7342-7370, 44, <https://pubs.rsc.org/en/content/articlehtml/2015/cs/c5cs00376h>.

* cited by examiner

| | FCC Yields | | Incremental Yields in FCC using 2.5% Black Oil | | 2016-2021 Avg Price cents/gal |
|---|---|---|---|---|---|
| | HT Feed + 5% Black Oil | HT Feed + 2.5% Black Oil | Black Oil | HT Feed (with Black Oil calculated out) | |
| Propylene, vol% | 12.59 | 12.14 | 29.75 | 11.69 | 141.91 |
| Propane, vol% | 2.94 | 3.08 | -7.39 | 3.22 | 66 |
| *Total C3, vol%* | *15.53* | *15.22* | *27.36* | *14.91* | |
| Isobutane, vol% | 9.03 | 9.68 | -15.7 | 10.33 | 90.15 |
| Norm. Butane, vol% | 1.88 | 2.01 | -3.07 | 2.14 | 92.6 |
| Butylenes, vol% | 12.06 | 11.31 | 40.64 | 10.56 | 223.02 |
| *Total C4, vol%* | *22.97* | *23.00* | *21.87* | *23.03* | |
| C5-450 Gasoline, vol% | 62.85 | 63.82 | 26.04 | 64.78 | 157.76 |
| 450-680 LCO, vol% | 10.75 | 10.75 | 10.77 | 10.75 | 171.67 |
| 680+Slurry, vol% | 3.49 | 3.24 | 13.02 | 2.99 | 111.5 |
| | 178.08 | 177.82 liquid product value | 188.37 | 177.01 cents/gal | |
| | 160.27 | 161.59 feed cost | | | |
| | 17.81 | 16.24 cents/gal margin | | | |
| | 7.48 | 6.82 $/bbl margin | | | |

Please note: (1) the incremental yields attributable to "Black Oil" in FCC using 2.5% black oil were obtained by calculating the incremental yields between FCC yields obtained by using a 5% black oil-containing feedstock and a 2.5% black oil-containing feedstock; and (2) the incremental yields attributable to "HT feed" using 2.5% black oil were calculated based on (i) the FCC yield obtained from a feedstock containing HT Feed + 2.5% Black and (ii) the incremental yields attributable to "Black Oil" in FCC using 2.5% black oil as noted above.

FIGURE 2

FCC FEED ADDITIVE FOR PROPYLENE/BUTYLENE MAXIMIZATION

CROSS REFERENCE TO RELATED APPLICATION

The present patent application is based upon and claims the benefit of provisional patent application No. 62/505,196, filed on May 12, 2017.

FIELD OF THE INVENTION

This invention involves a process for maximizing the production of light olefins by means of a fluidized catalytic cracking unit (FCC). Specifically, light olefin production through an FCC wherein high quality feed oil is processed with a catalyst and an additional feed additive is injected to improve propylene and butylene yields.

BACKGROUND OF THE INVENTION

Light olefins have increased in value dramatically in recent years for the reason that they are building blocks for many end products, such as polyethylene and polypropylene. Past production of polypropylene was obtained by steam cracking light naphtha. The main products produced by steam cracking are ethylene and gasoline with propylene and other light olefins obtained as by products. Propylene production from steam crackers depends upon the operating rates of the steam cracker and the type of feed stock supplied. Past steam cracking technology produced propylene from heavy liquid cracking. However, most modern steam crackers use ethane-based feed leading to less propylene being produced. As such, steam cracking alone cannot satisfy the demand for propylene and there is a need of new technology to produce additional propylene to bridge the gap between supply and demand. Attempts to reconfigure the steam cracker found that there was not the flexibility of operation and also there was high energy consumption, both of which were economically unacceptable.

Attempts to reconfigure FCC units to maximize the production of propylene and light olefins created energy savings and flexibility of operations. The use of catalysts in the FCC process is found to lower the temperature for catalytic naphtha cracking, thus resulting in less energy consumption. It has been found that the addition of catalysts to improve selectivity of propylene greatly enhances the yield of propylene and other olefins. It has further been found that coke formed during the cracking process is removed by the catalyst. The catalyst is in turn decoked through catalyst regeneration. It has also been discovered that the FCC is one of the most flexible processes in refining. An FCC unit can be readily adjusted to changes in feed quality through modifications of catalyst and operating conditions.

Zeolite-based heterogeneous catalysts are commonly used in the allocation of aromatic hydrocarbons. A good example of a zeolite-based catalyst is zeolite ZSM-5.

It is an object of the invention to provide a process wherein normal hydro treated FCC gas oil feed stock is processed by a normal FCC to provide high yields of olefinic gasoline.

Shape selective catalyst additives (ZSM-5) uses the olefinic gasoline to generate olefinic LPG rating resulting in an increase in propylene yield by a factor of 2 to 3. However, ZSM-5 does not effect the same increases in butylene.

It is an object of the invention to provide a process to generate more butylene selective yields, while maintaining propylene yields.

SUMMARY OF THE INVENTION

This innovation focuses on a FCC feed additive and its effects in production of olefinic LPG when injected using a separate nozzle on an FCC riser. Specifically, a small amount (up to 5 volume percent) of sweet vacuum residue (black oil) in the FCC feed in conjunction with the use of shape selective zeolite technology improves propylene and butylene yields significantly. The FCC feed additive of black oil results in observed incremental propylene (C3) and butylene (C4) olefin yields of 29.75 and 40.64 volume percent respectively. These yields are dramatically greater when compared to C3 and C4 olefin yields from the base sweet gas oil of 11.69 and 10.56 volume percent respectively.

BRIEF DESCRIPTION OF THE DRAWINGS

FIG. 2 is a table of data supporting the incremental propylene yields and incremental butylene yield of the process of this invention.

DESCRIPTION OF THE INVENTION

Figure 1:
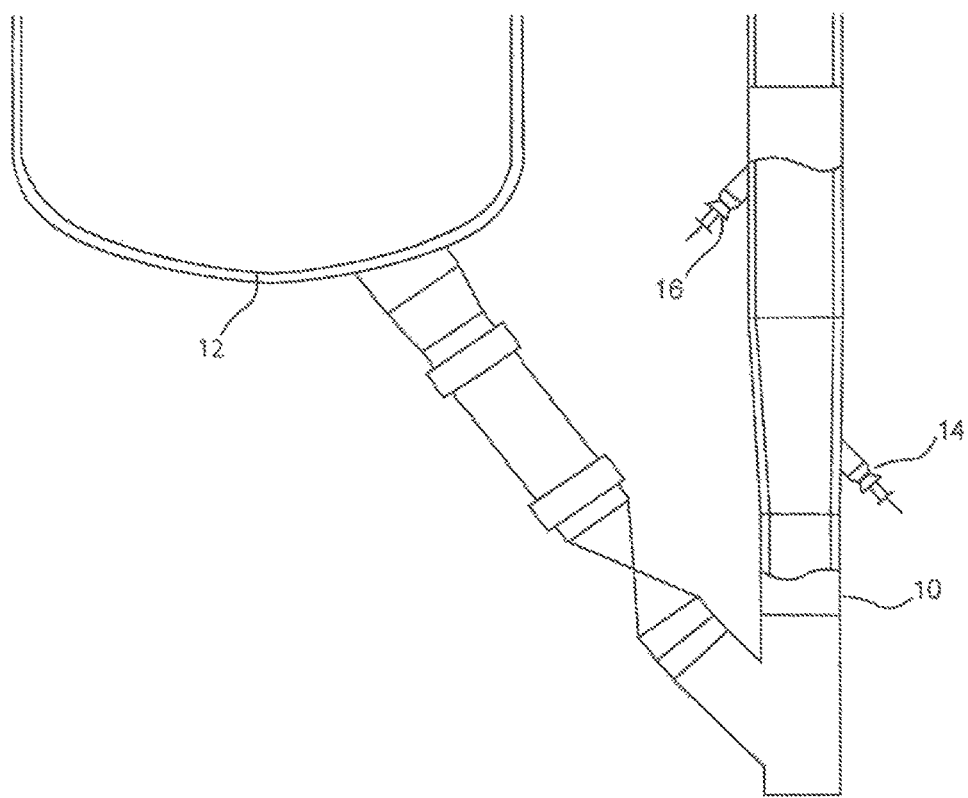
FIG. 1 is a partial sectional sketch showing the reactor riser of the present invention.

Co-processing sweet vacuum residue (black oil) alongside sweet gas oil in FCC units is well known in the industry. Such processing has been generally attractive due to the low feed stock costs associated with the alternative disposition (heavy fuel oil or similar) of sweet vacuum residue. However, the properties of sweet vacuum residue make it unattractive as a whole feed to an FCC.

This invention relates to the process wherein sweet vacuum residue is injected into the reactor riser via a separate feed nozzle. Viewing FIG. 1, the regenerated catalyst is fed from a catalyst regenerator 12 into the bottom of the reactor riser where it meets with the hydrotreated high quality gas oil being injected low in the reactor riser 10. High quality gas oil is injected into the riser 10 via feed nozzle 14. As the catalyst and high quality gas oil rise through the reactor riser black oil is added via a separate feed nozzle 16 (up to 5 volume percent). This creates incremental gasoline containing a very high concentration of olefins (approximately 80% by volume). Gasoline olefins are the feed stock for shape selective zeolite technology (ZSM-5) used in the generation of LPG olefins from FCC units. FCC units utilizing significant amounts of ZSM-5 along with the addition of black oil have produced incremental C3 and C4 olefin yields calculated to be 29.75 and 40.64 volume percent respectively. These volumes and yields are significantly higher than C3 and C4 olefin yields solely from based sweet gas which are 11.69 and 10.56 volume percent respectfully. The term "incremental yield" is defined as $Y' = [Y_{blend} - (1-X)Y_{base}]/X$, where $Y_{blend}$ is the yield of the blended feedstock (e.g. sweet gas oil+black oil), $Y_{base}$ is the yield of the base feedstock (e.g. sweet gas oil), and X is the weight fraction of the blend component. The incremental yield, Y' is the change in yield due to the addition of the blend component (e.g. black oil), normalized by the weight fraction of the blend component.

|  | 5% Black Oil | 2.5% Black Oil | Incremental Yields | | 2016-2021 Avg. Price |
|---|---|---|---|---|---|
|  |  |  | Black Oil | HT Feed | cents/gal |
| Propylene, vol % | 12.59 | 12.14 | 20.75 | 11.09 | 141.91 |
| Propane, vol % | 2.94 | 3.08 | −2.39 | 3.22 | 55 |
| Total C3, vol % | 15.53 | 15.22 | 27.36 | 14.91 |  |
| Isobutane, vol % | 9.03 | 9.68 | −15.7 | 10.33 | 90.15 |
| Norm. Butane, vol % | 1.88 | 2.01 | −3.07 | 2.14 | 92.6 |
| Butylenes, vol % | 12.06 | 11.31 | 40.64 | 10.56 | 223.02 |
| Total C4, vol % | 22.97 | 23.00 | 21.87 | 23.03 |  |
| C5-450 Baseline, vol % | 62.85 | 63.82 | 26.04 | 64.78 | 157.76 |
| 450-680 LCO, vol % | 10.75 | 10.75 | 10.77 | 10.75 | 171.67 |
| 680+ Slurry vol % | 3.49 | 3.24 | 15.02 | 2.09 | 111.5 |
|  | 178.08 | 177.82 liquid product value | 188.37 | 177.01 cents/gal |  |
|  | 100.27 | 161.59 feed cost |  |  |  |
|  | 17.81 | 16.24 cents/gal margin |  |  |  |
|  | 7.48 | 6.82 $/bbl margin |  |  |  |

FIG. 2 is a table of data supporting the incremental propylene yields and incremental butylene yield of the process of this invention.

Due to the high value of olefinic LPG products and low cost of the black oil, this results in improved FCC unit margin. Using 5 year average long term price forecast values. FCC margin with 5% black oil feed is $0.66/bbl higher than with 2.5% black oil in FCC Feed.

While black oil is a small percentage (0-5 vol %) of the total FCC feed, these impacts still shift the overall FCC C4 olefinicity by over 3%. By comparison, a significant change in FCC fresh catalyst composition at different FCC unit specifically aimed at improving C4 olefinicity has resulted in similar C4 olefinicity impacts (~5%),

|  | 5% Black Oil | 2.5% Black Oil |
|---|---|---|
| C4 Olefinicity | 52.5% | 49.2% |
| C3 Olefinicity | 81.1% | 79.8% |

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. A process for increasing the yields of propylene and butylene during the production of olefinic LPG in a fluidized catalytic cracking (FCC) unit, comprising the steps of:
   injecting a sweet gas oil blended with shape selective catalyst additives into a riser of the FCC unit;
   injecting via a separate nozzle a sweet vacuum residue for blending with the sweet gas oil and the shape selective catalyst additives wherein a percent volume of sweet vacuum residue being injected through the separate nozzle ranges from 1% to 5% with respect to a volume of the sweet gas oil; and
   producing a product stream comprising gasoline and the olefinic LPG, wherein an observed incremental propylene yield is 29.75 volume percent, and wherein an observed incremental butylene yield is 40.64 volume percent.

2. The process of claim 1 wherein the high concentration of olefins can be up to 80% by volume.

3. The process of claim 1 wherein the sweet vacuum residue consists of a heavy fuel oil.

4. The process of claim 1 wherein the sweet vacuum residue consists of a black oil.

* * * * *

UNITED STATES PATENT AND TRADEMARK OFFICE
CERTIFICATE OF CORRECTION

PATENT NO. : 10,435,339 B2
APPLICATION NO. : 15/976296
DATED : October 8, 2019
INVENTOR(S) : Nikolas Larsen et al.

It is certified that error appears in the above-identified patent and that said Letters Patent is hereby corrected as shown below:

In the Drawings

Replace Figure 2 with the attached Figure 2.

Signed and Sealed this
Twenty-eighth Day of January, 2020

Andrei Iancu
*Director of the United States Patent and Trademark Office*

|  | FCC Yields | Incremental Yields in FCC using 2.5% Black Oil | | 2016-2021 Avg Price cents/gal |
|---|---|---|---|---|
|  | HT Feed + 5% Black Oil | HT Feed + 2.5% Black Oil | Black Oil | HT Feed |  |
| Propylene, vol% | 12.59 | 12.14 | 29.75 | 11.69 | 141.91 |
| Propane, vol% | 2.94 | 3.08 | -2.39 | 3.22 | 66 |
| Total C3, vol% | 15.53 | 15.22 | 27.36 | 14.91 |  |
| Isobutane, vol% | 0.03 | 9.68 | -15.7 | 10.33 | 90.15 |
| Norm. Butane, vol% | 1.88 | 2.01 | -3.07 | 2.14 | 92.4 |
| Butylenes, vol% | 13.06 | 11.31 | 40.64 | 10.56 | 223.02 |
| Total C4, vol% | 22.97 | 23.00 | 21.87 | 23.03 |  |
| C5-450 Gasoline, vol% | 62.85 | 63.82 | 26.04 | 64.78 | 157.76 |
| 450-680 LCO, vol% | 10.75 | 10.75 | 10.77 | 10.75 | 171.67 |
| 680+ Slurry, vol% | 3.49 | 3.24 | 13.02 | 2.99 | 111.5 |
|  | 178.68 | 177.82 liquid product value | 188.37 | 177.01 cents/gal |  |
|  | 160.27 | 161.59 feed cost |  |  |  |
|  | 17.81 | 16.24 cents/gal margin |  |  |  |
|  | 7.48 | 6.82 $/bbl margin |  |  |  |

Please note: (1) the incremental yields attributable to "Black Oil" in FCC using 2.5% black oil were obtained by calculating the incremental yields between FCC yields obtained by using a 5% black oil-containing feedstock and a 2.5% black oil-containing feedstock; and (2) the incremental yields attributable to "HT feed" using 2.5% black oil were calculated based on (i) the FCC yield obtained from a feedstock containing HT Feed + 2.5% Black and (ii) the incremental yields attributable to "Black Oil" in FCC using 2.5% black oil as noted above.

FIGURE 2